United States Patent [19]
Kleber et al.

[11] 4,173,679
[45] Nov. 6, 1979

[54] LIQUID THERMOSTABLE PHOSPHORIC ACID ESTERS FOR THE FIBER CONDITIONING

[75] Inventors: Rolf Kleber, Neu-Isenburg; Winfried Ehrl, Neuotting, both of Fed. Rep. of Germany

[73] Assignee: Hoechst Aktiengesellschaft, Fed. Rep. of Germany

[21] Appl. No.: 862,516

[22] Filed: Dec. 20, 1977

[30] Foreign Application Priority Data

Dec. 24, 1976 [DE] Fed. Rep. of Germany ....... 2658862

[51] Int. Cl.$^2$ .......................... C07F 9/02; C11C 3/00; A23J 7/00
[52] U.S. Cl. .................................. 428/375; 260/403; 427/175; 252/8.9
[58] Field of Search ........................ 260/403; 252/8.9; 427/175; 428/365, 375

[56] References Cited

U.S. PATENT DOCUMENTS

| | | | |
|---|---|---|---|
| 2,345,734 | 4/1944 | Dickey et al. | 260/403 X |
| 3,004,056 | 10/1961 | Nunn et al. | 260/403 X |
| 3,273,667 | 9/1966 | Burgkirchen | 260/403 |
| 3,901,929 | 8/1975 | Cote | 260/403 |

*Primary Examiner*—John F. Niebling
*Attorney, Agent, or Firm*—Connolly and Hutz

[57] ABSTRACT

Fiber conditioning agent containing a reaction product of polyphosphoric acid and an oxalkylate of $C_{8-18}$ alkyl- or alkenylcarboxylic acids with 1 to 22 ethylene oxide units and having a content of free polyethylene glycol of less than 2% by weight, the reaction product being present in acidic form or in the form of its alkali metal salts. These fiber conditioning agents are applied by conventional methods. They show good antistatic properties, are stable to heat and show good lubricating and sliding properties.

3 Claims, No Drawings

LIQUID THERMOSTABLE PHOSPHORIC ACID ESTERS FOR THE FIBER CONDITIONING

It is known to use organic phosphoric acid esters as conditioning agents and antistatic agents in the fiber-preparing and fiber-processing industry (cf. Linder, Tenside, Textilhilfsmittel, Waschrohstoffe, 1964, volume II, pages 1616 et seq., page 1607). These esters may be prepared by reacting hydroxyl groups-containing compounds, for example alcohols, or ethylene oxide addition products with phosphoric acid hydroxychloride. The products thus obtained, however, have a high portion of phosphoric acid trisesters, which have a clearly defavorable influence on the antistatic properties. Phosphoric acid esters may further be prepared by reacting the above compounds with diphosphoric acid pentoxide (cf. U.S. Pat. Nos. 3,004,056 and 3,004,057), this process yielding substantially phosphoric acid mono- and -diesters. The phosphoric acid esters prepared in said manner certainly have obviously better antistatic properties than those based on phosphorus hydroxychloride, but are less thermostable, that is to say, they are perceptibly volatile at a temperature higher than 200° C. Moreover they are present in a pasty form which is difficult to handle and they are difficult to dissolve in water.

Owing to the very high production rates in the modern fiber industry and to the high temperatures occuring there is the need for thermostable fiber conditioning agents, which should be easy to handle.

It has now been found that fiber conditioning agents fulfilling said requirements may be obtained by esterifying oxalkylated alkane-carboxylic acids with polyphosphoric acid. The subject of the present invention, consequently, are fiber conditioning agents which are obtained by reacting polyphosphoric acid with oxalkylates prepared from $C_{8-18}$ alkyl- or alkenylcarboxylic acids and 1 to 22, preferably of from 8 to 18, mols of ethylene oxide. The starting compound used is commercial polyphosphoric acid having a content of from 80 to 90%, preferably of from 83 to 85%, of $P_2O_5$. Suitable oxalkylates are those which derive from alkyl- or alkenylcarboxylic acids or from mixtures thereof which have of from 8 to 18 carbon atoms, acids which may be manufactured on an industrial scale, for example coconut fatty acid, tallow fatty acid, oleic acid, being preferred. Said acids are oxethylated with 1 to 22, preferably with 8 to 18, mols of ethylene oxide according to known processes. The oxalkylates should have a content of free polyethylene glycol of less than 2%.

The products of the invention are prepared in the following manner: oxethylated carboxylic acid is introduced first and polyphosphoric acid is slowly added dropwise while stirring. The reaction temperature is maintained below 100° C., suitably in the range of from about 40° to 50° C. Both starting components are used in the following molar proportions: the quantity of oxalkylate ranges of from 3 to 3.5 mols, preferably is 3.2 mols, and the quantity of polyphosphoric acid ranges of from 2 to 2.5 mols, preferably is 2.25 mols, calculated on $P_2O_5$. Upon completion of the reaction there is obtained a homogeneous fluid solution consisting of from about 75 to 80% of the corresponding orthophosphoric acid monoester.

The reaction product obtained showing an acidic reaction may be readily diluted with water and be used directly as fiber conditioning agent. Preferably, however, the reaction mixture is previously neutralized with bases, for example sodium and potassium hydroxide, ammonia, alkylolamines or soda. The products thus obtained which mainly consist of phosphoric acid monoester show an excellent activity as antistatic fiber conditioning agents having favorable lubricating and sliding properties, for natural and preferably for synthetic fibers, for example polyester, polyamide, polyurethane, cellulose acetate, polyacrylonitrile, in particular as texturizing agents in the preparation of polyester fibers. They may be used alone or together with usual fiber conditioning agents, for example lubricants based on ester and mineral oil, emulsifiers, agents for effecting a compactness of the thread and others. The amount applied of the phosphoric acid esters on the fibers is in the range of from 0.1 to 3% by weight, preferably of from 0.3 to 1% by weight, calculated on the weight of the fiber. The esters are applied in a 5 to 25% by weight solution in the form of salts, according to the generally known methods, by spraying, dipping, padding or by means of lick rollers. They may alternatively be applied by spraying in undiluted form.

The above-described phosphoric acid esters based on polyphosphoric acid have the advantage that they are highly thermostable and good antistatic fiber conditioning agents and that they are fluid liquids of low viscosity even in undiluted form, which can be easily applied.

The following examples illustrate the invention:

EXAMPLE 1

2000 g of a washed reaction product of 1 mol of coconut-fatty acid and 10 mols of ethylene oxide having a content of polyethylene glycol of 0.4% are first introduced into a flask provided with a stirrer. 320 g of polyphosphoric acid (containing 84% of $P_2O_5$) are added while stirring, at room temperature, within 30 minutes and stirring is continued at 40° C. for 6 hours. After cooling to room temperature, a solution of 408 g of KOH in 203 g of $H_2O$ is slowly added dropwise to the homogeneous solution of the free ester acids. The final product has a pH of 7.3 (1% in $H_2O$) and a solids content of 90%.

EXAMPLE 2

Example 1 is repeated using 2000 g of coconut fatty acid, which have been oxethylated with 8 mols of ethylene oxide per mol of fatty acid (molecular weight 538), washed and dried and have a polyethylene glycol content of 1.0%. When reacting the starting product with 373 g of polyphosphoric acid (content of $P_2O_5$ 84%) there is obtained a reaction product which after addition of 475 g of KOH in 236 g of water has a pH of 7.5 in 1% aqueous solution and a solids content of 89%.

EXAMPLE 3

According to the procedure of Example 1 2000 g of oleic acid.10 AeO which have been washed and dried (polyethylene glycol content 0.1%, molecular weight 722) are reacted with 276 g of polyphosphoric acid and neutralized with 368 g of KOH in 248 g of water. The final product has a pH of 7.6 in 1% aqueous solution and a solids content of 91%. The product is liquid, its solution in water at 25° C. is clear and it has a thermostabilityof 4% (loss by evaporation at 220° C. after heating for 1 hour).

EXAMPLE 4

According to Example 1 2000 g of oleic acid.15 AeO, which have been washed and dried (PEG content 0.3%, molecular weight 942) are reacted with 219 g of polyphosphoric acid and neutralized with 292 g of KOH in 197 g of water. The final product is liquid and has a pH of 7.4 in 1% aqueous solution and a solide content of b 93%. The product dissolves in water yielding a clear solution at 20° C. Its thermostability is 3%.

COMPARATIVE TEST:

The following products are compared:
(a) according to Example 1 (according to the invention)
(b) according to Example 2 (according to the invention)
(c) reaction product of $P_2O_5$ with lauryl alcohol.4 Aeo, neutralized with KOH (U.S. Pat. No. 3,004,056) (comparison)
(d) reaction product of lauryl alcohol with $P_2O_5$ according to (c) (comparison)
(e) reaction product of nonyl phenol.2 AeO $P_2O_5$, neutralized with KOH (U.S. Pat. No. 3,004,056) (comparison)
(f) reaction product of $P_2O_5$ with iso-tridecyl alcohol (according to U.S. Pat. No. 3,004,056) as sodium salt (comparison)

(1) The following examinations were carried out:

| appearance | thermostability* (%) | soluble in $H_2O$ at |
|---|---|---|
| (a) liquid | (90%) | 3 | 20° C. |
| (b) liquid | (89%) | 5 | 20° C. |
| (c) hard wax | (75%) | 40 | 80° C. |
| (d) hard wax | (75%) | 45 | 90° C. |
| (e) liquid | (100%) | 19 | 50° C. |
| (f) hard wax | (75%) | 42 | 90° C. |

*loss by evaporation at 220° C. after heating for 1 hour.

(2) The products (a) to (f) were applied from an aqueous solution onto a PA 6 filament (dtex 200 f 40) by means of a lick roller with an amount of 0.7% of active substance and the threads were dried at 70° C. The threads were tested for their sliding friction in the apparatus which has been described in German Offenlegungsschrift No. 2,335,675. The values found of the dynamic friction and of the antistatic properties were as follows:

| friction | antistatic properties* |
|---|---|
| (a) 0.200–0.220 | 4 |
| (b) 0.190–0.210 | 3 |
| (c) 0.230–0.250 | 150 |
| (d) 0.022–0.240 | 750 |
| (e) 0.300–0.350 | 100 |
| (f) 0.290–0.310 | 1000 |

*antistatic values in megohm (22° C./65 % of relative humidity).

(3) The products (a) to (f) were applied onto a bundle of spun PES filaments with an amount of 0.5% of active substance and the filaments were drawn to dtex 167 f 32 and twisted. During the texturizing process which followed, the following observations could be made:

| heating temperature 220° C. |
|---|
| (a) no fuming and dropping |
| (b) no fuming and dropping |
| (c) considerable smoking |
| (d) enormous smoking |
| (e) smoking and dropping |
| (f) considerable smoking |

What is claimed is:

1. Fiber conditioning agent containing a reaction product of polyphosphoric acid and an oxalkylate of $C_{8-18}$ alkyl- or alkenylcarboxylic acids with 1 to 22 ethylene oxide units and having a content of free polyethylene glycol of less than 2% by weight, the reaction product being present in acidic form or in the form of its alkali metal salts.

2. Fiber conditioning agent as claimed in claim 1, containing an alkali metal salt of a reaction product of polyphosphoric acid and an oxalkylate of coconut or tallow fatty acid with 8 to 18 ethylene oxide units and having a content of free polyethylene glycol of less than 2% by weight.

3. A process for the conditioning of fibers and filaments during their synthesis and processing which consists of applying onto the fibers or filaments a reaction product of polyphosphoric acid and an oxalkylate of $C_{8-18}$ alkyl- or alkenylcarboxylic acids with 1 to 22 ethylene oxide units and having a content of free polyethylene glycol of less than 2% by weight, the reaction product being present in acidic form or in the form of its alkali metal salts.

* * * * *